United States Patent [19]

O'Reilly

[11] Patent Number: 5,885,582
[45] Date of Patent: Mar. 23, 1999

[54] EXTRACT FROM THE LEAVES OF GINKGO BILOBA

[75] Inventor: Joseph O'Reilly, Glouthaune, Ireland

[73] Assignee: Montana Limited, County Cork, Ireland

[21] Appl. No.: 952,893

[22] PCT Filed: May 31, 1996

[86] PCT No.: PCT/IE96/00034

§ 371 Date: Jan. 15, 1998

§ 102(e) Date: Jan. 15, 1998

[87] PCT Pub. No.: WO96/38160

PCT Pub. Date: Dec. 5, 1996

[30] Foreign Application Priority Data

Jun. 1, 1995 [IE] Ireland ........................... 950392

[51] Int. Cl.$^6$ .............. A61K 35/78; A61K 7/48
[52] U.S. Cl. .......................... 424/195.1; 514/25
[58] Field of Search .................. 424/195.1; 514/25

[56] References Cited

U.S. PATENT DOCUMENTS

| | | | |
|---|---|---|---|
| 4,981,688 | 1/1991 | Ayroles et al. | 424/195.1 |
| 5,077,046 | 12/1991 | Tanaka et al. | 424/195.1 |
| 5,322,688 | 6/1994 | Schwabe | 424/195.1 |
| 5,389,370 | 2/1995 | O'Reilly et al. | 424/195.1 |
| 5,399,348 | 3/1995 | Schwabe | 424/195.1 |
| 5,512,286 | 4/1996 | Schwabe | 424/195.1 |

FOREIGN PATENT DOCUMENTS

| | | |
|---|---|---|
| 62-255433 | 11/1987 | Japan . |
| 95 15172 | 6/1995 | WIPO . |
| 96 25142 | 8/1996 | WIPO . |

*Primary Examiner*—Herbert J. Lilling
*Attorney, Agent, or Firm*—Darby&Darby

[57] ABSTRACT

An extract from *Ginkgo biloba* is prepared by separating a lipid fraction, mixing with an alcohol, extracting the alcoholic solution with an organic solvent to remove neutral lipids, and the alcoholic solution is dissolved in a solvent and applied to a chromatographic column. A number of extracting media are applied to the chromatographic column to extract various fractions. The particular fractions of interest for incorporation into topical compositions have characteristics of cerebrosides or digalactosyldiglycerides.

49 Claims, No Drawings

EXTRACT FROM THE LEAVES OF GINKGO BILOBA

The invention relates to a new extract from the leaves of *Ginkgo biloba* and its method of preparation.

Certain extracts from the leaves of *Ginkgo biloba* are widely used for the therapy of peripheral and cerebral arterial circulatory disturbances. Various processes for preparing such extracts are described for example in DE-B -1767098, DE-B2117429, EP-A 0 324 197, EP-A 330 567 and EP-A 0 436 129.

The invention also provides a method for preparing a glycolipid extract from *Ginkgo biloba* leaves comprising the steps of:
  extracting the leaves with an organic solvent;
  separating the extract from the leaves;
  cooling the extract to precipitate a lipid fraction;
  recovering the lipid fraction from the extract;
  mixing the lipid fraction with an alcohol;
  removing insoluble material;
  extracting the alcoholic solution with an organic solvent to remove neutral lipids;
  treating the concentrated alcoholic solution with a number of extracting media;
  purifying the extracting medium containing a desired fraction; and
  substantially removing the associated extracting medium from the desired fraction to provide a concentrated extract.

The process of the invention is a highly efficient extraction process for extracting desired extracts, such as cerebrosides and especially digalactosyldiglycerides from the leaves of *Ginkgo biloba*. These extracts have applications in topical compositions.

In general terms in the process of the invention; the leaves of *Ginkgo biloba* are first extracted with an organic solvent such as acetone/water and the resulting solution is concentrated, for example, by evaporation and cooled. The solution is then filtered and a $C_1$–$C_3$ alcohol such as ethanol is added to the precipitate. The solution is agitated and again filtered. The filtrate is adjusted with water and extracted with a suitable organic solvent especially a non polar solvent such as heptane. The particular advantage of extraction with a non polar solvent prior to application to a chromatographic column is that the solvent removes a substantial proportion, typically 30%, of the dry extract. As a result the amount of desired extract, particularly digalactosyldiglycerides, is increased. The aqueous alcoholic phase is then evaporated to dryness, or evaporated and filtered and an organic solvent is added. The resulting solution is filtered, and then purified by chromatographic separation using solvent extraction media.

Preferably the organic solvent in which the concentrated alcoholic solution in dissolved is the same as a first extracting medium applied to the column. This optimises the chromatographic process.

In a preferred embodiment of the invention the concentrated alcoholic solution from which neutral lipids have been removed is treated with at least two different extracting media. The advantage of this feature is in facilitating the targeted extraction of a desired fraction from the material applied to the column.

Preferably at least one of the extracting media is an organic solvent.

In a preferred embodiment of the invention the organic solvent is a mixture of acetone and toluene. We have found that this solvent is particularly advantageous in targeting the extracts of interest. The strength of the mixture depends on the extract being targeted. Preferably the organic solvent in 5% to 80% acetone/toluene. In one case the organic solvent is 20% to 80% acetone toluene, most preferably 40% to 50% acetone/toluene.

In another case where ginkgolic acids, which are generally undesirable, are to be extracted the acetone/toluene is preferably 5 to 30%, especially approximately 20%.

In another embodiment of the invention one of the extracting media with which the concentrated alcoholic solution from which neutral lipids have been removed is treated is a mixture of an organic solvent and an alcohol. Preferably the alcohol is a $C_1$ to $C_3$ alcohol, especially ethanol. Preferably also in this case the solvent is acetone. The extracting medium may be 5% to 85% ethanol/acetone depending on the target extract. In one case it is 8% ethanol/acetone and in another 80% ethanol/acetone.

One of the extracting media may be acetone which is again a useful solvent for target extracts.

In a preferred embodiment of the invention the alcoholic solution is concentrated prior to treatment with the extracting medium/media. Typically the alcoholic solution is concentrated by evaporation.

In one embodiment of the invention a desired fraction obtained by extraction is concentrated, redissolved and reprocessed through the chromatographic column to produce a more concentrated desired fraction. Preferably the medium containing the desired fraction is purified by treating with charcoal and filtering the desired extract to remove the charcoal.

In one preferred embodiment of the invention the concentrated alcoholic solution is dissolved in 40% acetone toluene, applied to a chromatographic column and 20% acetone/toluene, 40% acetone/toluene, acetone and 8% ethanol/acetone were applied sequentially to the column. In this case preferably the fraction extracted by the acetone was concentrated, redissolved in 40% acetone/toluene and reprocessed through the column. One of the extracts in this case has characteristics of digalactosyldiglycerides and another has characteristics of cerebrosides.

In another preferred embodiment of the invention the concentrated alcoholic solution is dissolved in 80% acetone/toluene, applied to a chromatographic column and 80% acetone/toluene, acetone, and 80% ethanol acetone were applied sequentially to the column. In this case preferably the fraction extracted by the acetone was concentrated, washed and dried. The extract in this case has characteristics of digalactosyldiglycerides.

In a further preferred embodiment of the invention after treating the alcoholic solution with an organic solvent to remove neutral lipids the alcoholic solution is concentrated and filtered. In this case preferably the precipitate is dissolved in 50% acetone/toluene, applied to a chromatographic column, and 50% acetone/toluene and 8% ethanol/acetone are applied sequentially to the column. Preferably the ethanol/acetone fraction is concentrated, redissolved in 70% acetone/toluene and reprocessed through the chromatographic column. The extract in this came has characteristics of digalactosyldiglycerides at particularly high levels of purity, greater than 80% and in some cases approximately 95%.

The invention also provides a topical composition including an extract of the invention.

The invention will be described in further detail with reference to the following examples.

EXAMPLE 1

Step 1
60 kg of finely milled *Ginkgo biloba* leaves were extracted with 500 l of a 60% acetone water mixture in a counter current extraction unit at a temperature of 55°–60° C.

The extract was separated from the leaves and was then concentrated by evaporation.

Step 2
The concentrate was cooled to 8°–10° C. and was retained at this temperature for 3 hours.

The lipids which precipitated were recovered by decanting.

The recovered lipids were then dissolved in an agitated solution of 2.9 kg of acetone and 0.7 kg of demineralised water. A further 30 kg of demineralised water was then added.

The solution was continuously agitated and cooled to 8°–10° C. and was retained for a minimum of 3 hours before being decanted.

Step 3
The wet decanted lipids from Step 2 were added to 80 kg of ethanol and agitated for 3 hours.

Insoluble material was removed by decanting.

Step 4
The ethanolic solution from Step 3 was adjusted to 12–15% water.

The solution was extracted with 60 l of Heptane.

The ethanol-water phase was evaporated to greater than 85% dry extract.

Step 5
The alcoholic solution containing the extract from Step 4 was dissolved in 40% acetone/toluene and retained at ambient temperature overnight.

This solution was filtered and was then applied to 18 kg of silica in a packed column. The following solvents were pumped through the column: -200 l 20% acetone/toluene, 400 l 40% acetone/toluene, 100 l acetone and 120 l 8% ethanol/acetone.

Step 6
The desired fraction extracted by the third extraction medium (acetone) applied to the column was evaporated and redissolved in 40% acetone/toluene and reprocessed through the column using the same conditions as above and three main fractions taken.

Step 7
Charcoal (1 part) was added to the desired acetone solution (10 parts Dry Extract) and the solution was agitated for 30 minutes and filtered. The resulting solution was evaporated giving 120 g of a green brown solid. This fraction was characterised using HPLC chromatography and a mass detection for identification.

The extract from which substantially all of the neutral lipids and ginkgolic acids were removed with the first (20% acetone/toluene) extracting solvent was analysed by HPLC analysis and exhibited three major peaks.

The first peak was characteristic of monogalactosyldiglycerides. The third peak was characteristic of digalactosyldiglycerides which are the preferred extract. The peaks eluting between the mono and digalactosyldiglycerides may be cerebroside in character.

The second of the three fractions obtained in Step 6 above contains greater than 70 to 80% of the material corresponding to the second major peak. This fraction may be cerebroside in character.

EXAMPLE 2

Step 1
35 kg of finely milled *Ginkgo biloba* leaves were extracted with 280 l of a 60% acetone water mixture in a counter current extraction unit a temperature of 55°–60° C.

The extract was separated from the leaves and was then concentrated by evaporation.

Step 2
The concentrate was cooled to 8°–10° C. and was retained at this temperature for 3 hours.

The lipids which precipitated were recovered by decanting.

The recovered lipids were then dissolved in an agitated solution of 1.4 kg of acetone and 1.0 kg of demineralised water. A further 18 kg of demineralised water was then added.

The solution was continuously agitated and cooled to 8°–10° C. and was retained for a minimum of 3 hours before being decanted.

Step 3
The wet decanted lipids from Step 2 were added to 34 kg of ethanol and agitated for 3 hours.

Insoluble material was removed by decanting.

Step 4
The ethanolic solution from Step 3 was adjusted to 12–15% water.

The solution was extracted with 40 l of Heptane.

The ethanol-water phase was evaporated to greater than 85% dry extract.

Step 5
The extract from Step 4 was dissolved in 80% acetone/toluene and retained at ambient temperature overnight.

This solution was filtered and was then applied to 18 kg of silica in a packed column. The following solvents were pumped through the column:- 140 l 80% acetone/toluene, 130 l acetone and 120 l 80% ethanol/acetone.

Step 6
The acetone fraction was evaporated and the resulting material washed several times with acetone. The semi solid was dried to give a pale yellow solid which was identified and quantified on HPLC analysis as digalactosyldiglycerides (45 g) at a purity of 95%.

The glyceride moiety of the digalactosyldiglycerides was identified by hydrolysis and gas chromatography analysis of the methyl esters.

C16:0 15.3%
C16:1 0.4%
C18:0 2.9%
C18:2 8.0%
C18:3 55.7%
Others 17.7%

EXAMPLE 3

Step 1
60 kg of finely milled *Ginkgo biloba* leaves were extracted with 500 l of a 60% acetone water mixture in a counter current extraction unit at a temperature of 55°–60° C.

The extract was separated from the leaves and was then concentrated by evaporation.

Step 2
The concentrate was cooled to 8°–10° C. and was retained at this temperature for 3 hours.

The lipids which precipitated were recovered by decanting.

The recovered lipids were then dissolved in an agitated solution of 2.9 kg of acetone and 0.7 kg of demineralised water. A further 30 kg of demineralised water was then added.

The solution was continuously agitated and cooled to 8°–10° C. and was retained for a minimum of 3 hours before being decanted.

Step 3

The wet decanted lipids from Step 2 were added to 80 kg of ethanol and agitated for 3 hours.

Insoluble material was removed by decanting.

Step 4

The ethanolic solution from Step 3 was adjusted to 12–15% water.

The solution was extracted with 60 l of Heptane.

The ethanol was evaporated and the resulting solution filtered.

Step 5

The precipitate from Step 4 was dissolved in 50% acetone/toluene and retained at ambient temperature overnight.

This solution was filtered and was then applied to 18 kg of silica in a packed column. The following solvent was pumped through the column:- 180 l 50% acetone/toluene, and 120 l 8% ethanol/acetone.

Step 6

The ethanol/acetone fraction was evaporated and redissolved in 70% acetone/toluene and reprocessed through the column.

Step 7

The desired fraction rich in digalactosyldiglycerides was evaporated to dryness to give a light brown solid. Precipitation with acetone yielded digalactosyldiglyceride.

The digalactosyldiglyceride and cerebroside extracts have shown activity in cosmetic and skin care applications.

The invention is not limited to the specific embodiments hereinbefore described, which may be varied in detail.

I claim:

1. A method for preparing an extract from *Ginkgo biloba* leaves comprising the steps of:
    extracting the leaves with a first organic solvent;
    separating the extract from the leaves;
    cooling the extract to precipitate a lipid fraction;
    recovering the lipid fraction from the extract;
    mixing the lipid fraction with an alcohol;
    removing insoluble material;
    extracting the alcoholic solution with a second organic solvent to remove neutral lipids and concentrate the alcoholic solution;
    treating the concentrated alcoholic solution with one or more of extracting media;
    purifying the extracting media containing a desired fraction; and
    substantially removing the associated extracting media from the desired fraction to provide a concentrated extract.

2. The method of claim 1 wherein the second organic solvent is a non polar solvent.

3. The method of claim 2 wherein the non polar solvent is heptane.

4. The method of claim 1 wherein the concentrated alcoholic solution is dissolved in a third organic solvent and the solution and the extracting media are passed through a chromatographic column.

5. The method of claim 4 wherein the third organic solvent is the same as the first extracting medium passed to the column.

6. The method of claim 1 wherein the alcoholic solution from which neutral lipids have been removed is treated with at least two different extracting media.

7. The method of claim 6 wherein at least one of the extracting media is an organic solvent.

8. The method of claim 7 wherein the organic solvent is a mixture of acetone and toluene.

9. The method of claim 8 wherein the organic solvent contains 5% to 80% acetone/toluene.

10. The method of claim 9 wherein the organic solvent contains from 20% to 80% acetone/toluene.

11. The method of claim 10 wherein the solvent contains 5% to 50% acetone/toluene.

12. The method of claim 6 wherein the concentrated alcoholic solution from which neutral lipids have been removed is treated with an extraction media which is a mixture of an organic solvent and an alcohol.

13. The method of claim 12 wherein the alcohol is a $C_1$ to $C_3$ alcohol.

14. The method of claim 13 wherein the alcohol is ethanol.

15. The method of claim 12 wherein the organic solvent is acetone.

16. The method of claim 12 wherein the extracting medium is a 5% to 85% ethanol/acetone mixture.

17. The method of claim 16 wherein one of the extracting media is an 8% to 80% ethanol/acetone mixture.

18. The method of claim 4 wherein one of the extracting media is acetone.

19. The method of claim 1 wherein the desired fraction is substantially removed by precipitation with an organic solvent.

20. The method of claim 1 wherein the alcoholic solution is concentrated prior to treatment with the extracting media.

21. The method of claim 20 wherein the alcoholic solution is concentrated by evaporation.

22. The method of claim 1 wherein the concentrated extract is redissolved and reprocessed through the chromatographic column to further concentrate the desired fraction.

23. The method of claim 22 wherein the concentrated extract is purified by treating with charcoal and filtering to remove the charcoal.

24. The method of claim 4 wherein the concentrated alcoholic solution is dissolved in a 40% acetone/toluene mixture, passed through a chromatographic column and, thereafter, a 20% acetone/toluene mixture, a 40% acetone/toluene mixture, acetone and an 8% ethanol/acetone mixture are passed sequentially through the column.

25. The method of claim 22 wherein the fraction extracted by the acetone is concentrated and redissolved in a 40% acetone/toluene mixture and reprocessed through the chromatographic column.

26. The method of claim 17 wherein the reprocessed extract has the characteristics of digalactosyldiglycerides.

27. The method of claim 25 wherein the reprocessed extract has the characteristics of cerebrosides.

28. The method of claim 4 wherein the concentrated alcoholic solution is dissolved in an 80% acetone/toluene mixture, passed through a chromatographic column and, thereafter, an 80% acetone/toluene mixture, acetone, and an 80% ethanol/acetone mixture are sequentially passed through the column.

29. The method of claim 28 wherein the fraction extracted by the acetone is concentrated, washed and dried.

30. The method of claim 29 wherein the fraction extracted by acetone has the characteristics of digalactosyldiglycerides.

31. The method of claim 1 wherein, after treating the alcoholic solution with the second organic solvent the concentrated alcoholic solution is filtered.

32. The method of claim 31 wherein the filtered precipitate is dissolved in a 50% acetone/toluene mixture, passed through a chromatographic column, and, thereafter, a 50% acetone/toluene mixture and an 8% ethanol/acetone mixture are sequentially passed through the column.

33. The method of claim 32 wherein the ethanol/acetone fraction is concentrated, redissolved in a 70% acetone/toluene mixture and reprocessed through the chromatographic column.

34. The method of claim 33 wherein the desired fraction has the characteristics of digalactosyldiglycerides.

35. An extract from *Ginkgo biloba* leaves prepared by the method of claim 1.

36. The extract of claim 35 which has characteristics of digalactosyldiglycerides.

37. The extract of claim 35 having a purity of greater than 80%.

38. The extract of claim 36 having a purity of approximately 95%.

39. The extract claim 35 which has characteristics of cerebrosides.

40. A topical composition comprising an extract prepared by the method of claim 1.

41. The method of claim 6 wherein one of the extracting media is acetone.

42. The method of claim 24 wherein the concentrated alcoholic solution is dissolved in an 80% acetone/toluene mixture, passed through a chromatographic column and, thereafter, an 80% acetone/toluene mixture, acetone, and an 80% ethanol/acetone mixture are sequentially passed through the column.

43. The method of claim 25 wherein the fraction extracted by the acetone is concentrated, washed and dried.

44. The method of claim 26 wherein the fraction extracted by acetone has the characteristics of digalactosyldiglycerides.

45. A composition comprising an extract predominantly comprising at least one of monogalactosyldiglycerides, cerebrosides and digalactosyldiglycerides prepared by the method of claim 1.

46. A composition according to claim 45 wherein the extract contains cerebrosides having a purity of at least 70% to 80%.

47. A composition according to claim 45 wherein the extract contains digalactosyldiglycerides having a purity of at least 80%.

48. A composition according to claim 45 wherein the extract contains digalactosyldiglycerides having a purity of at least 95%.

49. A composition according to claim 45 wherein the digalactosyldiglycerides has a glyceride moiety selected from C16:0, C16:1, C18:0, C18:2 and C18:3.

* * * * *